(12) United States Patent
Kefer

(10) Patent No.: US 7,445,620 B2
(45) Date of Patent: Nov. 4, 2008

(54) APPARATUS AND METHOD FOR PROTECTING NONTARGET TISSUE OF A PATIENT DURING ELECTROCAUTERY SURGERY

(75) Inventor: John Kefer, Cleveland, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 256 days.

(21) Appl. No.: 11/502,700

(22) Filed: Aug. 11, 2006

(65) Prior Publication Data
US 2007/0038208 A1 Feb. 15, 2007

Related U.S. Application Data

(60) Provisional application No. 60/707,389, filed on Aug. 11, 2005.

(51) Int. Cl.
A61B 18/18 (2006.01)
(52) U.S. Cl. .............. 606/42; 128/898; 606/34
(58) Field of Classification Search .......... 128/898; 606/32–52
See application file for complete search history.

(56) References Cited

U.S. PATENT DOCUMENTS

| | | | |
|---|---|---|---|
| 5,372,596 A | 12/1994 | Klicek et al. | |
| 5,766,165 A | 6/1998 | Gentelia et al. | |
| 5,951,546 A | 9/1999 | Lorentzen | |
| 6,053,912 A | 4/2000 | Panescu et al. | |
| 6,245,065 B1 * | 6/2001 | Panescu et al. | 606/40 |
| 6,391,024 B1 | 5/2002 | Sun et al. | |
| 6,488,679 B1 | 12/2002 | Swanson et al. | |
| 6,506,189 B1 | 1/2003 | Rittman, III et al. | |
| 6,530,922 B2 | 3/2003 | Cosman et al. | |
| 6,802,839 B2 | 10/2004 | Behl | |
| 7,101,365 B1 * | 9/2006 | Sharon | 606/9 |
| 2003/0060819 A1 * | 3/2003 | McGovern et al. | 606/41 |
| 2003/0199863 A1 * | 10/2003 | Swanson et al. | 606/40 |
| 2004/0054370 A1 | 3/2004 | Given | |
| 2005/0004570 A1 | 1/2005 | Chapman et al. | |
| 2005/0085806 A1 * | 4/2005 | Auge et al. | 606/32 |
| 2005/0203504 A1 * | 9/2005 | Wham et al. | 606/34 |

FOREIGN PATENT DOCUMENTS

| | | |
|---|---|---|
| WO | WO-90/02514 A1 | 3/1990 |
| WO | WO-94/10924 A1 | 3/1994 |
| WO | WO-94/23659 A1 | 10/1994 |

* cited by examiner

Primary Examiner—Henry M Johnson, III
(74) Attorney, Agent, or Firm—Tarolli, Sundheim, Covell & Tummino LLP

(57) ABSTRACT

An apparatus for protecting a nontarget body tissue of a patient during electrocautery surgery, an electrocautery probe being adapted to provide an electrical field to electrocauterize a target body tissue of the patient, includes a stent. The stent is adapted to detect the electrical field and to produce a field proximity signal in response to the detected electrical field. An electrical source provides electrical power to the probe. An electrical controller is adapted to receive the field proximity signal and to regulate electrical power to the probe in response to the field proximity signal. A method for protecting a nontarget body tissue of the patient during electrocautery surgery is also described.

20 Claims, 3 Drawing Sheets

APPARATUS AND METHOD FOR PROTECTING NONTARGET TISSUE OF A PATIENT DURING ELECTROCAUTERY SURGERY

RELATED PATENT APPLICATION

This application claims priority to the filing date of U.S. Provisional Application No. 60/707,389, filed Aug. 11, 2005, the subject matter of which is incorporated herein by reference.

TECHNICAL FIELD

The present invention relates to an apparatus and method for protecting a patient during electrocautery surgery and, more particularly, to a thermo-protective stent for protecting nontarget tissue of a patient from unintended thermal contact during electrocautery surgery.

BACKGROUND OF THE INVENTION

It is common for a surgeon to intubate a body lumen of a patient with a stent before engaging in surgery of target body tissues adjacent that body lumen. The stent placed in the body lumen is normally hollow to allow passage of bodily fluids therethrough for near-normal function of the body lumen during the surgery.

Use of a stent makes the nontarget tissues surrounding the body lumen easier to see and feel, so that the surgeon can avoid inadvertent contact with the nontarget tissues during the surgery. The term "nontarget tissues" is used herein to indicate body tissues susceptible to unintentional cauterization due to their proximity to the body tissues being targeted in the procedure.

In addition, the stent may provide rigidity or even some degree of formability to the nontarget tissues. These nontarget tissues are often obscured by fat or other surrounding support tissues, or may resemble another, target, body tissue. Additional rigidity and/or formability, when provided by the stent, will assist the surgeon with locating the nontarget tissues and/or keeping the nontarget tissues in their original position or in a desired alternate position, respectively.

For example, a conventional ureteric double-J stent is a thin, flexible, plastic tube with a retention curl on each end (each curl referred to as a "J"). This stent is designed to be atraumatically inserted into the ureter and pelvis of the kidney prior to abdominal and pelvic surgery to improve visible and tactile identification of the ureter, and may also be sufficiently stiff to help keep the ureter from shifting into the operative field. Such assistance with identification and positioning of any desired nontarget body tissue is particularly useful during electrocautery surgery.

Electrocautery tools use a controlled discharge of focused electricity from an electrified knife to burn/cut through target tissues in a controlled manner. If the probe is inadvertently brought within close proximity of a nontarget tissue, such as the ureter discussed above, the electrical charge emitted may inadvertently burn/damage the nontarget tissue along with the surrounding target tissue. This type of accidental damage can occur very quickly, perhaps even before the proximity of the nontarget tissue is noticed, and can result in complications to the patient such as discomfort, increased surgery time, and dysfunction of previously healthy tissues. Additional surgery may be required to correct accidental electrocautery damage to nontarget body tissues.

Accordingly, it is desirable to provide an apparatus and method of protecting nontarget tissues of a patient during electrocautery surgery.

SUMMARY OF THE INVENTION

In an embodiment of the present invention, an apparatus for protecting a nontarget body tissue of a patient during electrocautery surgery, an electrocautery probe being adapted to provide an electrical field to electrocauterize a target body tissue of the patient, is described. A stent is adapted to detect the electrical field and to produce a field proximity signal in response to the detected electrical field. An electrical source provides electrical power to the probe. An electrical controller is adapted to receive the field proximity signal and to regulate electrical power to the probe in response to the field proximity signal.

In an embodiment of the present invention, a method for protecting nontarget body tissue of a patient during electrocautery surgery is described. Electrical power is provided to a probe. The probe is adapted to provide an electrical field responsive to the electrical power and to electrocauterize a target body tissue. A stent is placed adjacent the nontarget body tissue. The stent is adapted to detect the electrical field and to produce a field proximity signal in response to the detected electrical field. The field proximity signal is received with an electrical controller. Electrical power to the probe is regulated in response to the field proximity signal.

BRIEF DESCRIPTION OF THE DRAWINGS

For a better understanding of the invention, reference may be made to the accompanying drawings, in which.

DESCRIPTION OF EMBODIMENTS

Figure 1:
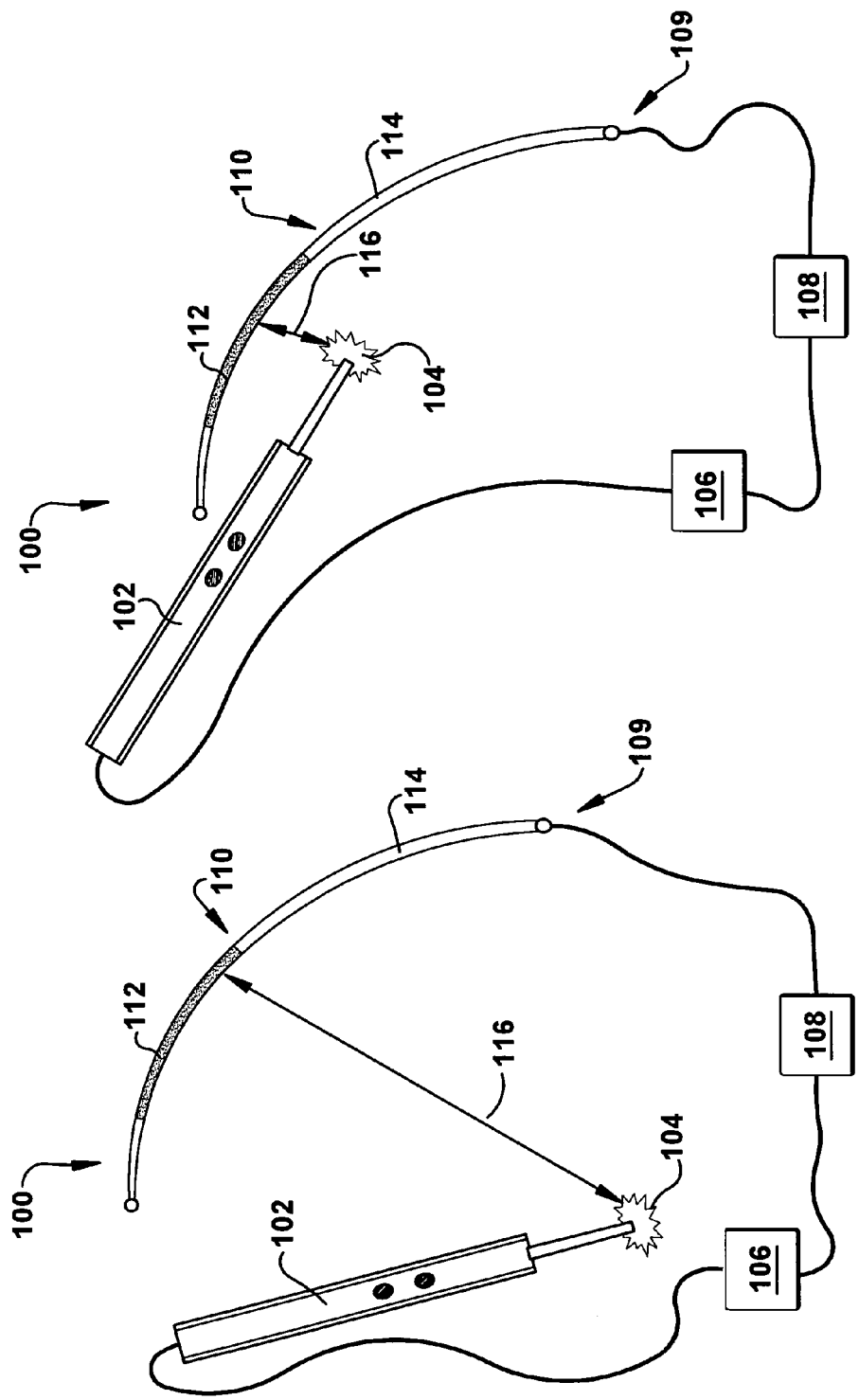
FIG. 1A is a schematic view of one embodiment of the present invention in a first condition.
FIG. 1B is a schematic view of the embodiment of FIG. 1A in a second condition.

In accordance with the present invention, FIG. 1A depicts an apparatus 100 for protecting a nontarget body tissue of a patient during electrocautery surgery. The apparatus 100 will be discussed herein as protecting a nontarget ureter of a patient during an electrocautery colorectal, OB/GYN, or urologic procedure, but could be used to protect any nontarget body tissue during any surgical procedure at any location in the body. For example, nontarget body tissues could include small and large intestines, blood vessels, the bladder, the stomach, the trachea, the larynx, the esophagus, and other organs, body structures, and the like.

The apparatus 100 includes a probe 102 being adapted to provide an electrical field 104. Such probes 102 are commonly used for electrocauterizing a target body tissue of a patient and many types of such probes, such as a Bovie electrocautery knife, are commercially available.

An electrical source 106 provides electrical power to the probe 102 from a building power supply, generator, uninterruptible power source, or the like. An electrical controller 108 regulates electrical power to the probe 102 from the electrical source 106.

A sensing structure 109 provides an input to the electrical controller 108. The sensing structure 109 could be a shield, wire mesh, sheet, tube, forceps, or any other structure as desired, and should be designed for placement adjacent or within the nontarget body tissue. The sensing structure 109 will be discussed herein as being a stent 110, or a portion thereof, intended to intubate a nontarget body lumen, such as a ureter, of the patient. The stent 110 may have a tubular cross-section enclosing a hollow stent lumen (not shown), the stent lumen allowing flow of bodily fluids of the patient therethrough. Alternatively, the stent 110 may have a solid cross-section but allow flow of bodily fluids of the patient around the stent (i.e., between the stent and the inner wall of the body lumen). In other applications, the stent 110 may selectively permit the flow of body fluids within that body lumen in another manner.

The stent 110 is adapted to detect the electrical field 104 and to produce a field proximity signal (FPo) in response to the detected electrical field. The field proximity signal should be indicative of the distance between the stent 110 and the electrical field 104 and is used to help prevent the electrical field from getting close enough to the stent 110 to damage the nontarget body tissue located adjacent the stent 110. While an electrical field 104 does not have a crisp border, a sensor sensitivity can be chosen for the stent 110 which detects electrical energy above a "background" level and thus imposes an artificial border or edge on the electrical field sufficient for the purposes of the present invention.

The stent 110 may include a metallic feature assisting with detection of the electrical field 104. For example, the metallic feature may be formed by a thin, even microscopic, metallic coating 112 on all or part of an outer surface 114 of the stent. The metallic coating 112 may also or instead be located on an inner surface (not shown) of the stent 110, when the stent includes a stent lumen.

The field proximity signal indicates a distance between the stent 110 and the electrical field 104. The distance may be indicated using an absolute or relative value, frequency, intensity, polarity, or other property of the field proximity signal. The electrical controller 108 is adapted to receive the field proximity signal and to regulate electrical power to the probe 102 in response to the field proximity signal. Therefore, the apparatus 100 may help prevent electrocautery damage of nontarget tissue by reducing electrical power (thus reducing the size and/or strength of the electrical field 104) when the stent 110 senses that the electrical field 104 is approaching closely enough to the nontarget tissue to risk damage thereto. Optionally, a value of the field proximity signal FPo is inversely proportional to a distance 116 between the probe 102 and the electrical field 104, and will be discussed as such herein. When the proportionality is reversed, the rising/falling direction changes of the signals and comparisons thereof will be reversed from those in this description.

The probe 102 may be adapted to operate at any of a plurality of electrical power levels. The electrical field 104 will have a different sensed size at each of these power levels, with the electrical field becoming stronger as more electrical power is provided to the probe 102 and smaller as less electrical power is provided to the probe. Therefore, the stent 110 should not merely sense the distance to the probe 102, because a "safe" distance between the probe 102 and the stent 110 will vary with the size of the electrical field 104 caused by the electrical power provided to the probe.

In order to protect the nontarget tissue, the electrical controller 108 monitors the field proximity signal from the stent 110. When the value of the field proximity signal (FPo) reaches or exceeds a predetermined threshold field proximity signal (FPt) value indicating that the electrical field 104 is within a first predetermined distance of the stent 110, the electrical controller 108 reduces the electrical power provided to the probe 102. This reduction may be a complete shutdown or may be a lowering to a predetermined limited power level based upon the initial electrical power level, the rate of change of the field proximity signal, or any other suitable factor.

When the threshold field proximity signal operation results in a lowering of power instead of a shutdown, the electrical controller 108 should continue to monitor the field proximity signal FPo. When the value of the field proximity signal (FPo) reaches or exceeds a predetermined shutdown field proximity signal (FPs) value indicating that the electrical field 104 is within a second predetermined distance of the stent 110, the electrical controller 108 discontinues the electrical power provided to the probe 102. The second predetermined distance should be less than the first predetermined distance. In this manner, both a "coarse", or relatively high-power, and a "fine" or relatively low-power, mode can be provided automatically to help the surgeon efficiently and completely electrocauterize the target body tissue while avoiding damage to the nontarget body tissue.

Because the size of the electrical field 104 varies directly with the level of electrical power provided to the probe 102, the threshold field proximity signal (FPt) value may be related to the power level of the probe 102. That is, when the probe 102 is operating at a higher level of electrical power, the electrical controller 108 does not allow the electrical field 104 to approach as closely to the stent 110 as would be permitted if the probe 102 were operating at a lower level of electrical power. For example, the threshold field proximity signal value could have a directly proportional relationship with the power level of the probe 102.

Following this principle, if the electrical power to the probe 102 is increased suddenly while the distance between the probe 102 and the stent 110 stays substantially the same, the threshold field proximity signal value should also be increased quickly by the electrical controller 108. In this manner, the electrical controller 108 can discontinue electrical power to the probe 102 in a timely manner if the larger electrical field 104 based upon this new power level causes generation of a new field proximity signal value which reaches or exceeds the updated threshold field proximity signal value. The electrical controller 108 thus should update the threshold field proximity signal as needed, based upon changes in electrical power provided to the probe 102.

The threshold and/or shutdown field proximity signals (FPt and/or FPs) may be adjusted based upon the type of surgery, location of the stent 110 relative to the nontarget tissue, composition of the target, nontarget, and surrounding body tissues, or any other desired variables. However, the electrical controller 108 should include a "safe range" of values for the threshold and shutdown field proximity signals, outside of which operation of the apparatus is not permitted.

Similarly, the electrical controller 108 should read the field proximity signal as frequently as needed to detect changes in the distance 116 which might effect the nontarget tissue. If the field proximity signal returns a zero or nonsensical value when electrical power is being provided to the probe 102, the electrical controller 108 should promptly shut down power supply to the probe and indicate the apparent error.

It is contemplated that, once the electrical controller 108 diminishes or discontinues electrical power supplied to the probe 102, an alert (usually via a light or sound) will be triggered and some affirmative action (such as pressing a reset button) will have to be taken to restore the immediately previous level of electrical power to the probe. Under such a scheme, users of the apparatus will learn how close the probe 102 is permitted to approach the nontarget tissue and will be able to avoid later power reductions during the same or a similar procedure. In the alternative, the probe 102 could constantly emit a low level electrical field or another type of detectable emission, insufficiently powerful to damage the nontarget tissue, so that the field proximity signal or another signal indicative of the relative positions of the stent 110 and electrical field is generated at all times. In this latter scenario, electrical power to the probe 102 can be automatically restored when the probe is moved away from the stent 110.

Figure 2:
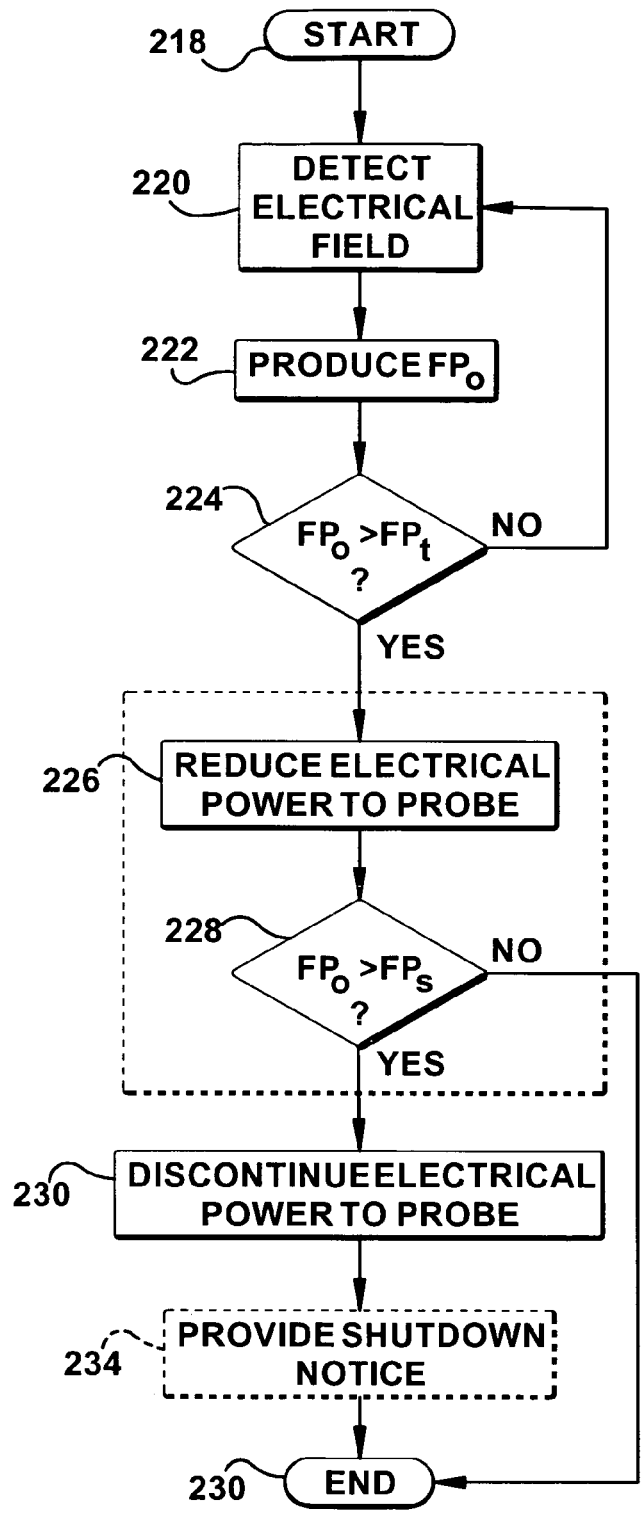
FIG. 2 is a flowchart of the operation of the embodiment of FIG. 1A.

FIG. 2 is a flowchart depicting the operation of the apparatus 100. This flowchart does not depict all of the internal routines required for the apparatus 100 to function suitably, but those additional routines may be readily determined by one of ordinary skill in the art for a desired application of the present invention.

Control of the present invention begins at start block 218. At first control block 220, the electrical field 104 is detected. Control then passes to second control block 222, where the field proximity signal (FPo) is produced. At first decision block 224, the value of the field proximity signal (FPo) is compared to the value of the threshold field proximity signal (FPt). If the field proximity signal is smaller that the threshold field proximity signal, control returns to first control block 220. FIG. 1A depicts an example of the relative positions of the stent 110 and electrical field 104 in such a first condition of operation.

If the field proximity signal is larger than the threshold field proximity signal, however, control proceeds to third control block 226, where electrical power to the probe 102 is reduced. FIG. 1B depicts an example of the relative positions of the stent 110 and electrical field 104 in this second, closer condition of operation. The value of the field proximity signal (FPo) is then compared to the value of the shutdown field proximity signal (FPs) at second decision block 228. If the field proximity signal is smaller that the shutdown field proximity signal, control proceeds to end block 230. Third control block 226 and second decision block 228 are enclosed within a dashed line to indicate that those two portions of the routine are optional.

When there is no provision for a lowered electrical power level, control proceeds directly from the "yes" branch of first decision block 224 to fourth control block 230. Alternatively, If the field proximity signal is determined to be larger than the shutdown field proximity signal at second decision block 228, control proceeds to fourth control block 230. At fourth control block 230, electrical power to the probe 102 is discontinued.

Control then proceeds to fifth control block 234, which is optional as indicated by the dashed border. At fifth control block 234, when present, a shutdown notice may be provided. After the apparatus alerts the user to the discontinuation of power, control passes to end block 230. The logic of FIG. 2 is repeated as often as needed for desired operation of the apparatus 100.

Figure 3:
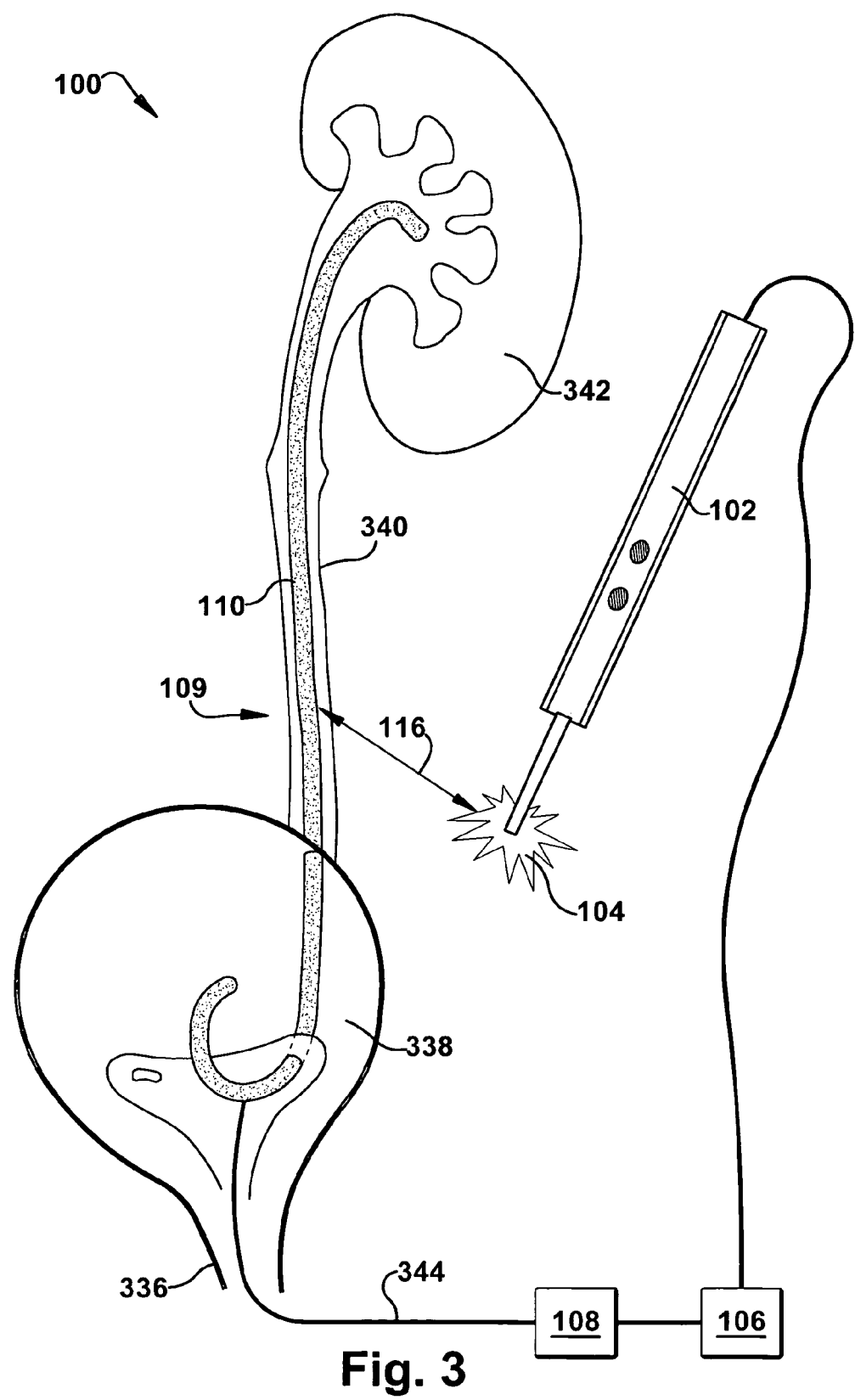
FIG. 3 is a schematic view of the embodiment of FIG. 1A in place in a body of a patient.

FIG. 3 depicts the apparatus 100 in place within a portion of a patient's body. In this example application, the stent 110 is a conventionally-shaped J-stent which has been inserted through the patient's urethra 336, through the bladder 338, up through the ureter 340, and into the kidney 342. A communication wire 344 trails from the stent 110 through the urethra 336 and carries the field proximity signal to the electrical controller 108 located outside the patient's body. The apparatus 100 shown in FIG. 3 operates similarly to those shown in FIGS. 1A, 1B, and 2, and the description above will not be repeated here.

The apparatus 100 may be helpful during laparoscopic procedures where the advantage of palpation of surrounding tissues is not available to avoid damage to nontarget tissues. By actively sensing proximity of the electrical field 104, as well as incorporating the power reduction/shutdown features described above, the apparatus 100 may allow electrocautery surgeries which were not previously practicable or feasible.

The apparatus 100 may also expand the thermoprotective sensing capacity of stents 110 or other sensing structures 110 inserted within or located adjacent other organs, such as the prostatic urethra to protect the verumontanum and urinary sphincter during transurethral resections of the prostate (TURP), the bladder during colorectal and OB/GYN procedures, the lungs and/or diaphragm during kidney cases, the colon during colorectal, general surgical procedures, OB/GYN, and urology cases, and the like.

While aspects of the present invention have been particularly shown and described with reference to the preferred embodiment above, it will be understood by those of ordinary skill in the art that various additional embodiments may be contemplated without departing from the spirit and scope of the present invention. For example, the probe 102 could be used as a conventional, nonpowered scalpel as well as an electrocautery device. The structures of the apparatus 100 could be made of any suitable materials. Multiple stents 110 and/or probes 102 could be provided by a single apparatus 100. Signals and/or power could be transferred among the elements of the apparatus 100 using wired or wireless connections, or a combination of the two. The electrical controller 108, or parts thereof, could be integrated into any or a combination of the stent 110, probe 102, and electrical source 106. The field proximity signal FPo could be a binary yes/no signal which would automatically equal the threshold field proximity signal (FPt) when present and prompt reduction of electrical power upon switching from the "no" to "yes" state. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. An apparatus for protecting a nontarget body tissue of a patient during electrocautery surgery, an electrocautery probe being adapted to provide an electrical field to electrocauterize a target body tissue of the patient, the apparatus comprising:
   a stent adapted to detect the electrical field and to produce a field proximity signal in response to the detected electrical field;
   an electrical source for providing electrical power to the probe; and
   an electrical controller adapted to receive the field proximity signal and to regulate electrical power to the probe in response to the field proximity signal.

2. The apparatus of claim 1, wherein the stent has a tubular cross-section enclosing a stent lumen, the stent lumen allowing flow of bodily fluids of the patient therethrough.

3. The apparatus of claim 1, wherein the stent has a solid cross-section and allows flow of bodily fluids of the patient between the stent and an inner wall of a body lumen.

4. The apparatus of claim 1, wherein the stent has a metallic feature assisting with detection of the electrical field.

5. The apparatus of claim 4, wherein the stent has an outer stent surface, the metallic feature being formed by a thin metallic coating on the outer stent surface.

6. The apparatus of claim 1, wherein the electrical controller reduces the electrical power provided to the probe responsive to the field proximity value reaching a threshold field proximity signal value, the threshold field proximity signal value being chosen to indicate that the probe is within a first predetermined distance of the stent.

7. The apparatus of claim 6, wherein the electrical controller discontinues the electrical power provided to the probe responsive to the field proximity value reaching a shutdown field proximity signal value, the shutdown field proximity signal value being chosen to indicate that the probe is within a second predetermined distance of the stent, the second predetermined distance being less than the first predetermined distance.

8. The apparatus of claim 7, wherein a value of the field proximity signal is inversely proportional to a distance between the electrical field and the stent.

9. The apparatus of claim 6, wherein the probe is adapted to operate at a plurality of electrical power levels, the threshold field proximity value being related to the power level of the probe.

10. The apparatus of claim 9, wherein the threshold field proximity value has a directly proportional relationship with the power level of the probe.

11. A method for protecting nontarget body tissue of a patient during electrocautery surgery, the method comprising the steps of:
providing electrical power to a probe, the probe being adapted to provide an electrical field responsive to the electrical power and to electrocauterize a target body tissue;
placing a stent adjacent the nontarget body tissue, the stent being adapted to detect the electrical field and to produce a field proximity signal in response to the detected electrical field;
receiving the field proximity signal with an electrical controller; and
regulating electrical power to the probe in response to the field proximity signal.

12. The method of claim 11, wherein the stent has a tubular cross-section enclosing a stent lumen, the stent lumen allowing flow of bodily fluids of the patient therethrough.

13. The method of claim 11, wherein the stent has a solid cross-section and allows flow of bodily fluids of the patient between the stent and an inner wall of a body lumen.

14. The method of claim 11, wherein the stent has a metallic feature assisting with detection of the electrical field.

15. The method of claim 14, wherein the stent has an outer stent surface, the metallic feature being formed by a thin metallic coating on the outer stent surface.

16. The method of claim 11, wherein the step of regulating electrical power to the probe responsive to the field proximity signal includes reducing the electrical power provided to the probe responsive to the field proximity value reaching a threshold field proximity signal value, the threshold field proximity signal value being chosen to indicate that the probe is within a first predetermined distance of the stent.

17. The method of claim 16, wherein the step of regulating electrical power to the probe responsive to the field proximity signal includes discontinuing the electrical power provided to the probe responsive to the field proximity value reaching a shutdown field proximity signal value, the shutdown field proximity signal value being chosen to indicate that the probe is within a second predetermined distance of the stent, the second predetermined distance being less than the first predetermined distance.

18. The method of claim 17, wherein a value of the field proximity signal is inversely proportional to a distance between the electrical field and the stent.

19. The method of claim 16, wherein the probe is adapted to operate at a plurality of electrical power levels, the threshold field proximity value being related to the power level of the probe.

20. The method of claim 19, wherein the threshold field proximity value has a directly proportional relationship with the power level of the probe.

* * * * *